United States Patent [19]

Schmidt et al.

[11] 4,417,059

[45] Nov. 22, 1983

[54] DIPHENYLAMINO AND INDOLYL SUBSTITUTED PYROMELLITIDES

[75] Inventors: Paul J. Schmidt, Sharonville; William M. Hung, Cincinnati, both of Ohio

[73] Assignee: Sterling Drug Inc., New York, N.Y.

[21] Appl. No.: 294,375

[22] Filed: Aug. 19, 1981

Related U.S. Application Data

[62] Division of Ser. No. 182,717, Aug. 29, 1980, Pat. No. 4,343,493.

[51] Int. Cl.$^3$ ............... C07D 405/04; C07D 405/14
[52] U.S. Cl. ........................... 548/456; 549/299
[58] Field of Search ................ 548/456; 549/299

[56] References Cited

U.S. PATENT DOCUMENTS

| | | | |
|---|---|---|---|
| 3,268,537 | 8/1966 | Gosnell et al. | 546/94 |
| 3,491,117 | 1/1970 | Lin | 282/27.5 |
| 4,168,378 | 9/1979 | Schmidt et al. | 546/101 |
| 4,182,714 | 1/1980 | Schmidt et al. | 548/440 |

OTHER PUBLICATIONS

Fawcett, Cassidy and Lin, Journal of Organic Chemistry, vol. 42, No. 17, 2929-2930, (1977).

*Primary Examiner*—Donald G. Daus
*Assistant Examiner*—D. B. Springer
*Attorney, Agent, or Firm*—Terrence E. Miesle; Lynn T. Fletcher; B. Woodrow Wyatt

[57] ABSTRACT

This invention relates to 3,7-bis(disubstituted aminophenyl- or indolyl)-3,7-bis(diphenylamino)pyromellitides, 3,5-bis(disubstituted aminophenyl- or indolyl)-3,5-bis(diphenylamino)pyromellitides and mixtures thereof useful as color formers, particularly in carbonless duplicating and thermal marking systems, which are prepared by the interaction of 2,5-bis(disubstituted aminophenyl- or indolyl)carbonyl-1,4-benzenedicarboxylic acids or 2,4-bis(disubstituted aminophenyl- or indolyl)carbonyl-1,5-benzenedicarboxylic acids and mixtures thereof with diphenylamines.

19 Claims, No Drawings

DIPHENYLAMINO AND INDOLYL SUBSTITUTED PYROMELLITIDES

CROSS REFERENCE TO PRIOR APPLICATIONS

This application is a division of copending application Ser. No. 182,717, filed Aug. 29, 1980 now U.S. Pat. No. 4,343,493.

BACKGROUND OF THE INVENTION (a) Field of the Invention

This invention relates to novel compounds classified in the field of organic chemistry as 3,7-bis[4-(disubstituted amino)phenyl]- or (indol-3-yl)-3,7-bis(diphenylamino)pyromellitides and 3,5-bis[4-(disubstituted amino)phenyl]- or (indol-3-yl)-3,5-bis(diphenylamino)pyromellitides and mixtures thereof useful as color precursors, particularly in the art of carbonless duplicating, for example, pressure-sensitive and thermal marking systems; to processes for preparing the pyromellitides; and to pressure-sensitive and thermal marking systems containing the pyromellitides.

(b) Description of the Prior Art

Several classes of organic compounds of widely diverse structural types are known to be useful as colorless precursors for carbonless duplicating systems. Among the more important classes, there may be named phenothiazines, for example, benzoyl leuco methylene blue; phthalides, for example, crystal violet lactone; fluorans, for example, 2'-anilino-6'-diethylaminofluoran and 2'-dibenzylamino-6'-diethylaminofluoran; and various other types of colorless precursors currently employed in commercially accepted carbonless copy systems. Typical of the many such systems taught in the prior art are those described in U.S. Pat. Nos. 2,712,507, 2,800,457 and 3,041,289 which issued July 5, 1955, July 23, 1957 and June 26, 1962, respectively. Many of the color formers in the prior art suffer one or more disadvantages such as low tinctorial strength, poor light stability, low resistance to sublimation, low susceptibility to copiability of the color-developed form in standard copying machines, for example, a Xerox ® copier, and low solubility of common organic solvents, the last-mentioned disadvantage thus requiring the use of specialized and expensive solvents in order to obtain microencapsulated solutions of sufficient concentration for use in pressure-sensitive copying machines.

The following items to date appear to constitute the most relevant prior art with regard to the instant invention.

U.S. Pat. No. 3,268,537, issued Aug. 23, 1966, discloses and claims a mixture of two isomeric pyromellitides, individually of the formulas

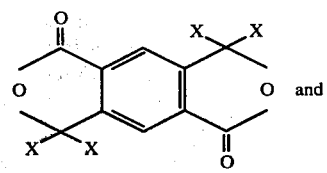

and

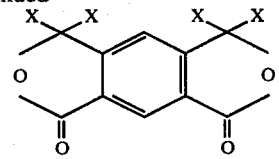

in which the Xs are selected from the group consisting of 9-julolidinyl, 4-aminophenyl and mono- and disubstituted 4-aminophenyl moieties. The compounds are disclosed to be colorless when dissolved in solvents normally used in carbonless duplicating systems and develop dark-colored images upon contact with suitable color-developing substances, for example, an acidic clay. The pyromellitides of this patent are prepared through the intermediates 2,5-[bis(4-dialkylaminophenyl)carbonyl]-1,4-benzenedicarboxylic acid and 2,4-[bis(4-dialkylaminophenyl)carbonyl]-1,5-benzenedicarboxylic acid, respectively.

U.S. Pat. No. 3,491,117, issued Jan. 20, 1970, discloses and claims a chromogenic pyromellitide selected from the group consisting of:

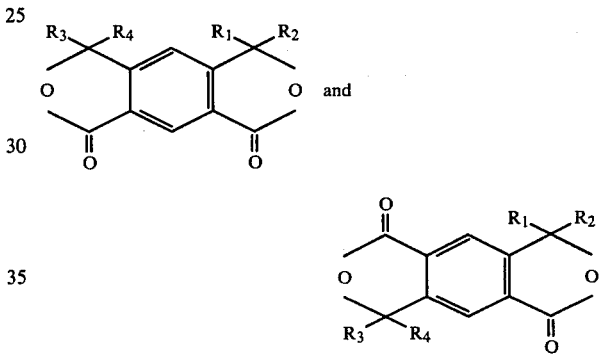

and mixtures thereof, where $R_1$, $R_2$, $R_3$ and $R_4$ consist of 1,2-dialkylindol-3-yl and p-dialkylaminophenyl groups wherein alkyl has less than five carbon atoms, such that as least two indolyl radicals are present in a cis relationship in compounds having a cis configuration and in a trans relationship in compounds having a trans configuration. The chromogenic compounds are disclosed as being useful in pressure-sensitive recording systems. The pyromellitides disclosed in this patent are prepared through 2,4-[bis(4-dialkylaminophenyl-, or indolyl)carbonyl]-1,5-benzenedicarboxylic acid and 2,5-[bis(4-dialkylaminophenyl-, or indolyl)carbonyl]-1,4-benzenedicarboxylic acid, respectively.

Fawcett, Cassidy and Lin in the Journal of Organic Chemistry 42 (17), 2929–2930 (1977) describe the preparation and physical characteristics of 3,3,5,5-tetraphenylpyromellitide and 3,3,7,7-tetraphenylpyromellitide from the interaction of 4,6-dibenzoylisophthalic acid or 2,5-dibenzoylterephthalic acid and benzene in the presence of aluminum chloride. No indication of utility for the compounds is given in the article.

Belgian Pat. No. 862,217, published June 22, 1978, which corresponds essentially to U.S. Pat. No. 4,168,378 and 4,182,714 which issued Sept. 18, 1979 and Jan. 8, 1980, respectively, in the names of Paul Joseph Schmidt and William Mo-Wei Hung, the inventors in the instant application, discloses a series of phthalides useful as color formers in pressure-sensitive carbonless duplicating systems, thermal marking systems and hectographic or spirit-reproducing copying systems and having the formula

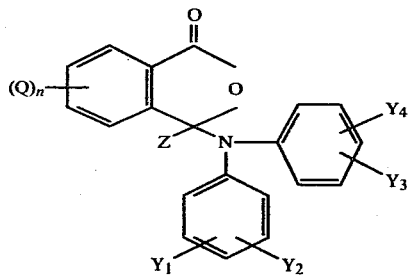

wherein Q is di-lower-alkylamino, nitro, halo or COX, where X is hydroxyl, benzyloxy, alkoxy having from 1 to 18 carbon atoms or OM where M is an alkali metal cation, an ammonium cation or a mono-, di- or trialkylammonium cation having from 1 to 18 carbon atoms; n is 0; or 1 when Q is di-lower-alkylamino, nitro or COX; or from 1 to 4 when Q is halo; $Y_1$, $Y_2$, $Y_3$ and $Y_4$ are the same or different and are hydrogen, halo, hydroxyl, lower-alkoxy, alkyl having from 1 to 9 carbon atoms, phenyl-lower-alkyl, $COOR_4$ or $NR_5R_6$, where $R_4$ and $R_5$ are hydrogen or lower-alkyl and $R_6$ is hydrogen, lower-alkyl, cycloalkyl having from 5 to 7 carbon atoms or lower alkanoyl; Z is chosen from the group consisting of

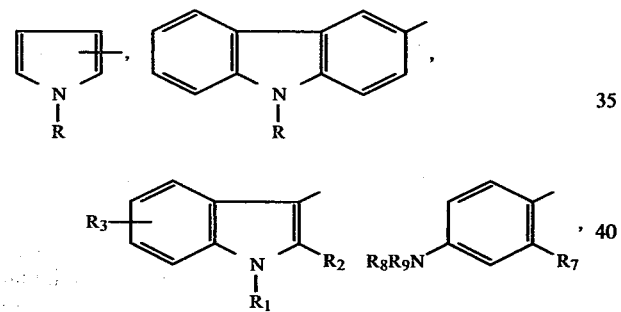

and 9-julolidinyl
in which R is hydrogen or non-tertiary alkyl having from 1 to 4 carbon atoms; $R_1$ is hydrogen or non-tertiary alkyl having from 1 to 18 carbon atoms; $R_2$ is hydrogen, phenyl or non-tertiary alkyl having from 1 to 4 carbon atoms; $R_3$ is hydrogen, non-tertiary alkyl having from 1 to 4 carbon atoms or non-tertiary alkoxy having from 1 to 4 carbon atoms; $R_7$ is hydrogen, halo, loweralkyl lower-alkoxy or di-lower-alkylamino; $R_8$ is lower-alkyl; and $R_9$ is lower-alkyl, benzyl, phenyl or phenyl substituted with a lower-alkyl or lower-alkoxy group.

SUMMARY OF THE INVENTION

The present invention in its composition of matter aspect, provides for novel pyromellitides selected from the group consisting of 3,7-bis(Y)-3,7-bis[N-(R, $R^o$-phenyl)-N-($R^1$, $R^2$-phenyl)amino]pyromellitides, 3,5-bis(Y)-3,5-bis[N-(R, $R^o$-phenyl)-N-($R^1$, $R^2$-phenyl)amino]pyromellitides, and mixtures thereof which are useful as color formers in pressure-sensitive duplicating systems and in thermal marking systems. The compounds have enhanced solubility in common organic solvents and develop colored images of good to excellent tinctorial strength which have good light stability.

In its process aspect, the invention relates to a process for preparing a series of pyromellitides selected from the group consisting of 3,7-bis(Y)-3,7-bis[N-(R, $R^o$-phenyl)-N-($R^1$, $R^2$-phenyl)amino]pyromellitide and 3,5-bis(Y)-3,5-bis-[N-(R, $R^o$-phenyl)-N-($R^1$, $R^2$-phenyl)amino]pyromellitide and mixtures thereof which comprises interacting an appropriate 2,5-bis(Y)-carbonyl-1,4-benzenedicarboxylic acid and 2,4-bis(Y)-carbonyl-1,5-benzenedicarboxylic acid, respectively and mixtures thereof with a N-(R, $R^o$-phenyl)-N-($R^1$, $R^2$-phenyl)amine in the presence of an anhydride of an alkanoic acid.

The present invention provides in its articles of manufacture aspect, pressure-sensitive carbonless duplicating systems and thermal marking systems each containing at least one color-forming substance comprising a pyromellitide selected from the group consisting of 3,7-bis-(Y)-3,7-bis[N-(R, $R^o$-phenyl)-N-($R^1$, $R^2$-phenyl)amino]pyromellitide and 3,5-bis(Y)-3,5-bis[N-(R, $R^o$-phenyl)-N-($R^1$, $R^2$-phenyl)amino]pyromellitide and mixtures thereof.

DETAILED DESCRIPTION INCLUSIVE OF THE PREFERRED EMBODIMENTS

More specifically, this invention in its composition of matter aspect, resides in the novel pyromellitides, which are particularly useful as colorless precursors in the art of carbonless duplicating and thermal marking, and which are selected from the group consisting of 3,7-bis(Y)-3,7-bis[N-(R, $R^o$-phenyl)-N-($R^1$, $R^2$-phenyl)amino]pyromellitide of the formula

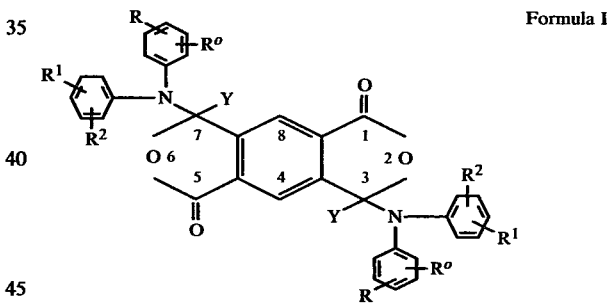

Formula I and 3,5-bis(Y)-3,5-bis-[N-(R, $R^o$-phenyl)-N-($R^1$, $R^2$-phenyl)-amino]pyromellitide of the formula

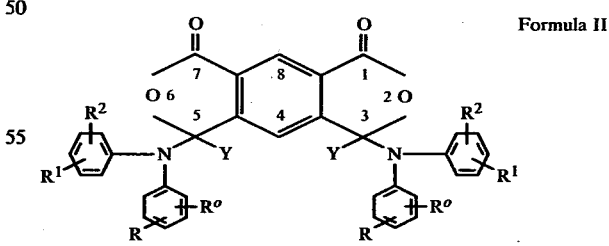

Formula II and mixtures thereof wherein R, $R^o$, $R^1$ and $R^2$ are the same or different and are selected from the group consisting of hydrogen, halo, hydroxyl, non-tertiary $C_1$ to $C_4$ alkoxy, non-tertiary $C_1$ to $C_9$ alkyl, COOZ and $NZ^1Z^2$ where Z and $Z^1$ are hydrogen or non-tertiary $C_1$ to $C_4$ alkyl and $Z^2$ is hydrogen, non-tertiary $C_1$ to $C_4$ alkyl, $C_5$ to $C_7$ cycloalkyl, $C_1$ to $C_4$ alkanoyl, phenylsulfonyl or phenylsulfonyl substituted by non-tertiary $C_1$ to $C_4$ alkyl; Y is a radical selected from the group consisting of

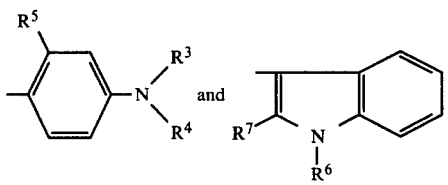

in which $R^3$ and $R^4$ are the same or different and are selected from the group consisting of non-tertiary $C_1$ to $C_4$ alkyl, benzyl and benzyl substituted by one or two of halo, $C_1$ to $C_4$ alkyl, $C_1$ to $C_4$ alkoxy or nitro; $R^5$ is selected from the group consisting of hydrogen, halo and non-tertiary $C_1$ to $C_4$ alkyl and non-tertiary $C_1$ to $C_4$ alkoxy; $R^6$ is selected from the group consisting of hydrogen and non-tertiary $C_1$ to $C_{12}$ alkyl; and $R^7$ is selected from the group consisting of hydrogen, non-tertiary $C_1$ to $C_4$ alkyl and phenyl.

In a first particular embodiment in accordance with its composition of matter aspect, the invention sought to be patented resides in the novel pyromellitides selected from the group consisting of 3,7-bis(1-$R^6$-2-$R^7$-indol-3-yl)-3,7-bis[N-(R, $R^o$-phenyl)-N-($R^1$, $R^2$-phenyl)amino]-pyromellitides and 3,5-bis(1-$R^6$-2-$R^7$-indol-3-yl)-3,5-[N-(R, $R^o$-phenyl)-N-($R^1$, $R^2$-phenyl)amino]-pyromellitides according to Formulas I and II and mixtures thereof wherein Y represents 1-$R^6$-2-$R^7$-indol-3-yl and R, $R^o$, $R^1$, $R^2$, $R^6$ and $R^7$ each have the same respective meanings given in Formulas I and II.

In a second particular embodiment in accordance with its composition of matter aspect, the invention sought to be patented resides in the novel pyromellitides selected from the group consisting of 3,7-bis(2-$R^5$-4-$NR^3R^4$-phenyl)-3,7-bis[N-(R, $R^o$-phenyl)-N-($R^1$, $R^2$-phenyl)amino]pyromellitide and 3,5-bis(2-$R^5$-4-$NR^3R^4$-phenyl)-3,5-bis[N-(R, $R^o$-phenyl)-N-($R^1$, $R^2$-phenyl)amino]pyromellitide according to Formulas I and II and mixtures thereof wherein Y represents 2-$R^5$-4-$NR^3R^4$-phenyl and R, $R^o$, $R^1$, $R^2$, $R^3$, $R^4$ and $R^5$ each have the same respective meanings given in relation to Formulas I and II.

In its process aspect, the invention sought to be patented resides in the process for preparing pyromellitides selected from the group consisting of 3,7-bis(Y)-3,7-bis[N-(R, $R^o$-phenyl)-N-($R^1$, $R^2$-phenyl)amino]-pyromellitide and 3,5-bis(Y)-3,5-bis[N-(R, $R^o$-phenyl)-N-($R^1$, $R^2$-phenyl)amino]pyromellitide and mixtures thereof which comprises interacting an appropriate 2,5-bis(Y)carbonyl-1,4-benzenedicarboxylic acid, and 2,4-bis(Y)carbonyl-1,5-benzenedicarboxylic acid, respectively and mixtures thereof having the respective formulas

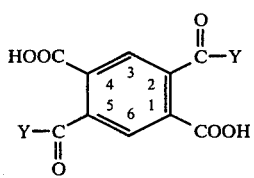 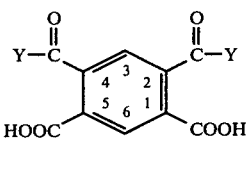

Formula III  Formula IV with a diarylamine having the formula

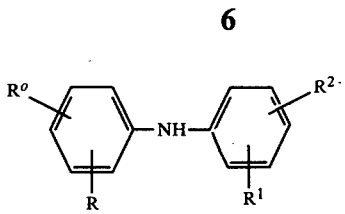

in the presence of the anhydride of an alkanoic acid having from 2 to 5 carbon atoms wherein R, $R^o$, $R^1$, $R^2$ and Y each have the same meanings given in relation to Formulas I and II.

In an article of manufacture aspect, the invention sought to be patented resides in a pressure-sensitive or thermal marking system comprising a support sheet coated with a layer containing as a color-forming substance a pyromellitide selected from the group consisting of 3,7-bis(Y)-3,7-bis[N-(R, $R^o$-phenyl)-N-($R^1$, $R^2$-phenyl)amino]pyromellitide and 3,5-bis(Y)-3,5-bis[N-(R, $R^o$-phenyl)-N-($R^1$, $R^2$-phenyl)amino]pyromellitide and mixtures thereof according to Formulas I and II wherein R, $R^o$, $R^1$, $R^2$ and Y each have the same respective meanings given relative to Formulas I and II.

In a particular embodiment in accordance with its article of manufacture aspect, the invention sought to be patented resides in a pressure-sensitive transfer sheet, adapted for use with a receiving sheet having an electron accepting layer, comprising a support sheet coated on one side with a layer of pressure-rupturable microcapsules; said microcapsules containing a liquid solution of a color-forming substance comprising at least one compound having Formula I or II.

Another embodiment in accordance with its article of manufacture aspect, resides in a heat responsive record material comprising a support sheet coated on one side with a layer containing a mixture comprising at least one color-forming compound having Formula I or II and an acidic developer arranged such that application of heat will produce a mark-forming reaction between the color-forming compound and the acidic developer.

As used herein the term "non-tertiary $C_1$ to $C_4$ alkyl", denotes saturated monovalent straight or branched aliphatic hydrocarbon radicals including methyl, ethyl, propyl, isopropyl, butyl, isobutyl, and the like. Further, the term "non-tertiary $C_1$ to $C_9$ alkyl" as used herein includes in addition to the aliphatic hydrocarbon radicals defined as $C_1$ to $C_4$ alkyl above, amyl, 1-methylbutyl, 3-methylbutyl, hexyl, isohexyl, heptyl, isoheptyl, octyl, isooctyl, 2-ethylhexyl, nonyl, 3-ethylheptyl, and the like. The term "non-tertiary $C_1$ to $C_{12}$ alkyl" as used herein includes the terms "non-tertiary $C_1$ to $C_4$ alkyl" and "non-tertiary $C_1$ to $C_9$ alkyl" as defined above, as well an n-decyl, n-undecyl, n-dodecyl, and the like.

As used herein the term "halo" includes chloro, fluoro, bromo and iodo. Chloro is the preferred halo substituent because of the relatively low cost and ease of preparation of the required chloro-substituted intermediates and because the other halogens offer no particular advantages over chloro. However the other above-named halo substituents are also satisfactory.

As used herein the term "cycloalkyl having from 5 to 7 carbon atoms" includes cyclopentyl, cyclohexyl and cycloheptyl.

The term "$C_1$ to $C_4$ alkanoyl" denotes saturated acyclic acyl groups having from 1 to 4 carbon atoms which may be straight or branched as exemplified by formyl, acetyl, propionyl, butyryl, isobutyryl, and the like.

The term "non-tertiary $C_1$ to $C_4$" alkoxy includes saturated, acyclic, straight or branch-chained groups such as methoxy, ethoxy, propoxy, isopropoxy butoxy, sec-butoxy and isobutoxy.

The novel compounds of Formulas I and II hereinabove are essentially colorless in the depicted form. When contacted with an acidic medium, for example, silica gel or one of the type ordinarily employed in pressure-sensitive carbonless duplicating systems such as silton clay or phenolic resins, the compounds of Formulas I and II develop a red-orange to an orange-colored image of good to excellent tinctorial strength, and possess an enhanced light stability over the prior art compounds, excellent xerographic copiability, and good resistance to sublimation. The compounds are thus highly suitable for use as colorless precursors, that is color-forming substances in pressure-sensitive carbonless duplicating systems. The red-orange to orange image developing color formers can be used alone or as toners in admixture with other color formers to produce developed images of a neutral shade which desirably are readily copiable by xerographic means. Moreover, the compounds of Formulas I and II have enhanced solubility over the prior art compounds in common and inexpensive organic solvents such as odorless mineral spirits, kerosene, vegetable oils and the like thereby avoiding the need for more expensive specialized solvents such as polyhalogenated or alkylated biphenyls which have ordinarily been used to prepare microencapsulated solutions of the color formers of the prior art.

The compounds of this invention may be incorporated in any of the commercially accepted systems known in the carbonless duplicating art. A typical technique for such application is as follows. Solutions containing one or more colorless precursor compounds of Formulas I and II, optionally in admixture with other color formers, in suitable solvents are microencapsulated by well-known procedures, for example, as described in U.S. Pat. No. 3,649,649. The microcapsules are coated on the reverse side of a transfer sheet with the aid of a suitable binder and the coated transfer sheet is then assembled in a manifold with the microcapsule coated side in contact with a receiving sheet coated with an electron accepting substance, for example, silton clay or phenolic resin. Application of pressure to the manifold such as that exerted by a stylus, typewriter or other form of writing or printing causes the capsules on the reverse side to rupture. The solution of the color former released from the ruptured microcapsules flows to the receiving sheet and on contact with the acidic medium thereon forms red-orange to orange-colored images of good tinctorial strength. It is, of course, obvious that variants of this mode of application can be utilized. For example, the receiving sheet in a manifold can alternatively be coated with the subject compounds and the acidic developing agent can be contained in microcapsules applied to the reverse side of the top sheet in the manifold; or the receiving sheet can be coated with a mixture containing both the acidic developing agent and the microencapsulated color former.

It has also been found that when the compounds of Formulas I and II are intimately mixed with an acidic developer of the type generally employed in thermal papers such as described in U.S. Pat. No. 3,539,375, that is, papers which produce a colored image when contacted with a heated stylus or heated type, for example, bisphenol A, heating of the mixture produces a colored image of varying shades from red-orange to orange depending on the particular compound of the invention employed. The ability of the compounds of Formulas I and II to form a deep color when heated in admixture with an acidic developer such as bisphenol A, makes them useful in thermal paper marking systems, either where an original or a duplicate copy is prepared by contacting the thermal paper with a heated stylus or heated type in any of the methods generally known in the art.

The best mode contemplated by the inventors of carrying out this invention will now be described so as to enable any person skilled in the art to which it pertains to make and use the same.

In accordance with the process aspect of this invention the 3,7-bis(Y)-3,7-bis[N-(R, R°-phenyl)-N-($R^1$, $R^2$-phenyl)amino]pyromellitides of Formula I and 3,5-bis-(Y)-3,5-bis-[N-(R, R°-phenyl)-N-($R^1$, $R^2$-phenyl)amino]pyromellitides of Formula II and mixtures thereof are obtained by interacting in approximately equimolecular proportions an appropriate benzenedicarboxylic acid, 2,5-bis[(Y)-carbonyl]-1,4-benzenedicarboxylic acid of Formula III, 2,4-bis[(Y)-carbonyl]-1,5-benzenedicarboxylic acid of Formula IV or mixtures thereof with an appropriate N-(R, R°-phenyl)-N-($R^1$, $R^2$-phenyl)amine of Formula V. The reaction is conveniently carried out in a dehydrating solvent, for example, an anhydride of a $C_2$ to $C_5$ alkanoic acid such as acetic anhydride at a temperature in the approximate range of 20°–60° C. for from approximately thirty minutes to forty-eight hours. The pyromellitides thus obtained can be isolated by several methods. One such method of isolation is to filter the pyromellitides from the reaction mixture if they are insoluble. An alternative method of isolation is to pour the reaction mixture into a miscible non-solvent for the product, for example, water or an alcohol such as isopropyl alcohol and filter the pyromellitides from the mixture. The pyromellitides, once isolated, can be purified by conventional means such as trituration or recrystallization from a suitable solvent. The isomeric mixtures of pyromellitides can, if desired, be separated by conventional means such as fractional crystallization or chromatography or simply and preferably used as mixtures in the practice of this invention.

The requisite bis(Y)carbonylbenzenedicarboxylic acids, 2,5-bis(Y)carbonyl-1,4-benzenedicarboxylic acid and 2,4-bis(Y)carbonyl-1,5-benzenedicarboxylic acid and mixtures thereof of Formulas III and IV required in the practice of this invention are conveniently prepared by the interaction of pyromellitic dianhydride with approximately two molecular proportions of a 1-$R^6$-2-$R^7$-indole or a 3-$R^5$-N-$R^3$-N-$R^4$-aniline wherein $R^3$, $R^4$, $R^5$, $R^6$, $R^7$ and Y each have the same meanings given in relation to Formulas III and IV. The reaction is usually carried out in the presence of a Lewis acid, for example, aluminum chloride, and with a diluent such as benzene, toluene or chlorobenzene at a temperature in the range of 0°–65° C. Alternatively, when indoles are interacted with pyromellitic anhydride, it is not necessary to use a Lewis acid and the reaction can be carried out in a $C_2$ to $C_5$ alkanoic acid, for example, acetic acid, and the product isolated by filtration. When a Lewis acid is used, the bis(Y)carbonylbenzenedicarboxylic acids are isolated by adding dilute mineral acid, for example, hydrochloric acid to the reaction mixture, filtering off the insoluble benzenedicarboxylic acid product, and washing the filter cake with water. The product is dissolved in a dilute aqueous alkali solution, treated with decolorizing charcoal and clarified. The dilute alkali solution of the product is made acid by the addition of a mineral acid, for example, hydrochloric acid and the benzenedicarboxylic acid product collected by filtration. The product may be purified by conventional means but is generally dried and used as is.

It will, of course, be appreciated that reaction of pyromellitic dianhydride with an indole or a N,N-dialkylaniline can produce isomers of a mixture of isomers of bis(indolyl- or dialkylaminophenyl)carbonylbenzenedicarboxylic acids. For example, reaction of pyromellitic dianhydride with indole can product a mixture of 2,4-bis(indolyl)carbonyl-1,5-benzenedicarboxylic acid and 2,5-bis(indolyl)carbonyl-1,4-benzenedicarboxylic acid. Similarly, reaction of pyromellitic anhydride with a N,N-dialkylaniline can produce an isomeric mixture of bis(dialkylaminophenyl)carbonylbenzenedicarboxylic acids. These mixtures of isomeric bis-(indolyl- or dialkylaminophenyl)carbonylbenzenedicarboxylic acids can be separated by conventional means such as fractional crystallization or chromatography. Alternatively, the isomeric mixtures can be reacted directly with appropriate N-(R, R°-phenyl)-N-($R^1$, $R^2$-phenyl)amines to produce isomeric mixtures of pyromellitides of Formulas I and II. Thus, reaction of a mixture of 2,5-bis(indolyl- or dialkylaminophenyl)carbonyl-1,4-benzenedicarboxylic acid and 2,4-bis(indolyl- or dialkylaminophenyl)carbonyl-1,5-benzenedicarboxylic acid with N-(R, R°-phenyl)-N-($R^1$, $R^2$-phenyl)amine will produce a mixture of the corresponding 3,7- and 3,5-bis(indolyl- or dialkylaminophenyl)-3,7- and 3,5-bis(diphenylamino)pyromellitides. The mixtures of pyromellitides can, if desired, be separated by conventional means or simply and preferably used as mixtures in the practice of this invention.

Indole and the substituted indoles required as intermediates of the carbonylbenzenedicarboxylic acid intermediates of Formulas III and IV wherein Y represents indolyl, form an old and well-known class of compounds which are readily obtained by conventional procedures well known in the art. The following compounds are exemplary of indoles useful in the practice of this invention.

Indole,
1-Methylindole,
2-Methylindole,
1,2-Dimethylindole,
1-Ethyl-2-methylindole,
1-Propyl-2-methylindole,
1-Butyl-2-methylindole,
1-Octyl-2-methylindole,
2-Ethylindole,
2-Ethyl-1-methylindole,
1-Isopropylindole,
2-Isopropylindole,
1-Isobutyl-2-methylindole,
1-Hexylindole,
2-Propylindole,
1-Isoamylindole and
1-(2-Ethylhexyl)-2-methylindole.

The 3-$R^5$-N-$R^3$-N-$R^4$-anilines, which are required as intermediates for the preparation of the carbonylbenzenedicarboxylic acid intermediates of Formulas III and IV wherein Y represents dialkylaminophenyl, form an old and well-known class of compounds which are readily obtained by conventional procedures well known in the art. The following compounds are exemplary of 3-$R^5$-N-$R^3$-N-$R^4$-anilines useful in the practice of this invention.

N,N-Dibutylaniline,
N,N-Diethyl-3-ethoxyaniline,
N,N-Diethyl-m-anisidine,
N,N-Dimethylaniline,
N-Benzyl-N-ethylaniline,
N,N-Diethyl-m-toluidine,
N,N-Diethylaniline,
N-Ethyl-N-methylaniline,
N-Benzyl-N-methylaniline,
N-Benzyl-N-propylaniline,
N,N-Dimethyl-3-bromoaniline,
N,N-Dibutyl-3-fluoroaniline,
N-Benzyl-N-methyl-3-ethylaniline,
N-Benzyl-3-butyl-3-iodoaniline,
N,N-Diisopropyl-3-chloroaniline,
N-Benzyl-N-sec-butylaniline,
N-N-Dipropylaniline,
N-Isopropyl-N-methylaniline,
N-Methyl-N-propylaniline,
N,N-Di-sec-butylaniline,
N,N-Diethyl-3-isopropylaniline,
N,N-Diisobutylaniline,
N,N-Dimethyl-m-toludine,
N-Isobutyl-N-ethylaniline,
N-Propyl-N-ethylaniline,
N-(4-Chlorobenzyl)-N-methylaniline,
N-(3-Bromobenzyl)-N-ethylaniline,
N,N-Di(4-methylbenzyl)aniline,
N-(4-Nitrobenzyl)-N-i-propylaniline,
N,N-Di(2,4-dichlorobenzyl)aniline,
N-(2,3-Dimethylbenzyl)-N-methylaniline,
N-(3-Nitrobenzyl)-N-sec-butylaniline.

The N-(R, R°-phenyl)-N-($R^1$, $R^2$-phenyl)amines which are required as starting materials in preparing the isomeric mixtures of pyromellitides of Formulas I and II of the invention belong to a well known class of compounds and are either commercially available or are readily obtained by conventional procedures well known in the art. The following compounds are exemplary of N-(R, R°-phenyl)-N-($R^1$, $R^2$-phenyl)amines useful in the practice of this invention.

Diphenylamine,
4-Ethoxy-N-phenylaniline,
3-Methyl-N-phenylaniline,
4-Isopropyl-N-phenylaniline,
4-Hydroxy-N-phenylaniline,
4,4'-Dioctyldiphenylamine,
3,3'-Diethyl-5,5'-dinonyldiphenylamine,
3-Chloro-N-phenylaniline,
4-Dimethylamino-N-phenylaniline,
Methyl-2-anilinobenzoate,
4,4'-Bis(dimethylamino)diphenylamine,
4-Acetamido-N-phenylaniline,
4,4'-Diacetamidodiphenylamine,
4-Octyl-4'-arylalkyldiphenylamine,
4,4'-Bis(diethylamino)diphenylamine,
4-Diethylamino-4'-dimethylaminodiphenylamine,
(4-Toluenesulfonamido)aniline.

The molecular structure of the compounds were assigned on the basis of the modes of synthesis and a study of their infrared and nuclear magnetic spectra.

The following examples will further illustrate the invention without, however, limiting it thereto.

EXAMPLE 1

A. A mixture of 6.4 g of pyromellitic dianhydride, 9.0 g of 1-ethyl-2-methylindole and 80.0 ml of toluene was stirred and cooled by means of an external ice-water bath to a temperature in the range of 0°–5° C. Over approximately ten minutes, 8.8 g of anhydrous aluminum chloride was added to the mixture while maintaining the temperature at 0°–5° C. After stirring approximately ten minutes at 0°–5° C., the reaction mixture was warmed to 45°–55° C. and stirring continued for an additional thirty minutes. To the reaction mixture there was added 5.0 ml of acetic anhydride and the mixture was stirred approximately thirty minutes at a temperature in the range of 50°–60° C. While maintaining a temperature in the range of 50°–60° C., 50.0 ml ofconcentrated hydrochloric acid diluted with 150.0 ml of water was added to the reaction mixture. Without cooling, the solid, which separated, was collected by filtration and washed with 50.0 ml of water. The water-wet filter cake was suspended in 50.0 ml of water with stirring and sufficient concentrated ammonium hydroxide was added gradually until the pH of the mixture was 10.0. The undissolved solid was removed by filtration and the filtrate was treated with decolorizing carbon and the resultant mixture filtered to remove the carbon. The filtrate was adjusted to pH 2.5 by the addition of three normal hydrochloric acid. The solid which formed was collected by filtration, washed with water and dried to obtain an isomeric mixture of [2,4-bis(1-ethyl-2-methylindol-3-yl)carbonyl]-1,5-benzenedicarboxylic acid (Formula III: $Y=1$-$C_2H_5$-2-$CH_3$-indol-3-yl) and [2,5-bis(1-ethyl-2-methylindol-3-yl)carbonyl]-1,4-benzenedicarboxylic acid (Formula IV: $Y=1$-$C_2H_5$-2-$CH_3$-indol-3-yl).

B. A mixture containing 1.0 g of the isomeric mixture [2,4-bis(1-ethyl-2-methylindol-3-yl)carbonyl]-1,5-benzenedicarboxylic acid and [2,5-bis(1-ethyl-2-methylindol-3-yl)carbonyl]-1,4-benzenedicarboxylic acid, from part A above, 2.2 g of di(4-octylphenyl)amine and 6.0 ml of acetic anhydride was stirred at a temperature in the range of 45°–550° C. for approximately thirty minutes. The reaction mixture was placed in a freezer for approximately fifteen minutes. After removing from the freezer, a red solid material was collected by filtration and the filtrate was added with stirring to approximately 25.0 ml water causing an oily red solid to agglomerate. The desired product was separated from the starting materials using a chromatographic column packed with 40–140 mesh silica gel employing isopropyl alcohol to elute the desired product through the column followed by a hexane wash of the column. The combined isopropyl alcohol and hexane mixture containing the desired product was evaporated to dryness to obtain a red-orange oil. The oil was dissolved in methyl alcohol and a trace of insolubles removed by filtration. The methanol solution was allowed to evaporate to dryness by standing at ambient temperature over a weekend to obtain 0.5 g of an isomeric mixture of 3,7-bis(1-ethyl-2-methylindol-3-yl)-3,7-bis[N,N-di(4-octylphenyl)-amino]pyromellitide (Formula I: $R=R^1=4$-$C_8H_{17}$; $R^o=R^2=H$; $Y=2$-$C_2H_5$-2-$CH_3$-indol-3-yl) and 3,5-bis(1-ethyl-2-methylindol-3-yl)-3,5-bis[N,N-di(4-octylphenyl)amino]pyromellitide (Formula II: $R=R^1=4$-$C_8H_{17}$; $R^o=R^2=H$; $Y=1$-$C_2H_5$-2$CH_3$-$CH_3$-indol-3-yl), an orange-red solid, which melted over the range 83°–92° C. The nuclear magnetic resonance spectrum was in accord with the assigned structure. An infrared maximum appeared at 1781 ($C=O$; s) $cm^{-1}$. A toluene solution of the product spotted on an acidic clay or a phenolic resin developed an orange-colored image.

EXAMPLE 2

A mixture containing 6.5 g of the isomeric mixture of [2,4-bis(1-ethyl-2-methylindol-3-yl)carbonyl]-1,5-benzenedicarboxylic acid and [2,5-bis(1-ethyl-2-methylindol-3-yl)carbonyl]-1,4-benzenedicarboxylic acid prepared in a manner similar to that described in Example 1, part A above, 20.0 ml of acetic anhydride, 5.0 ml of acetic acid and 4.7 g of diphenylamine was stirred for approximately 48 hours at ambient temperature. The solid that formed was collected by filtration, washed with isopropyl alcohol and dried to obtain 4.6 g of a pink-colored solid. This solid was reslurried twice in hot isopropyl alcohol, filtered and dried to obtain 3.7 g of an isomeric mixture of 3,7-bis(1-ethyl-2-methylindol-3-yl)-3,7-bis(diphenylamino)-pyromellitide (Formula I: $R=R^o=R^1=R^2=H$; $Y=1$-$C_2H_5$-2-$CH_3$-indol-3-yl) and 3,5-bis(1-ethyl-2-methylindol-3-yl)-3,5-bis(diphenylamino)pyromellitide (Formula II: $R=R^o=R^1=R^2=H$; $Y=1$-$C_2H_5$-2-$CH_3$-indol-3-yl), a pale pink-colored solid, which melted at 235°–238° C. The nuclear magnetic resonance spectrum was in accordance with the assigned structure. A maximum appeared in the infrared spectrum at 1770 ($C=O$; s) $cm^{-1}$. A toluene solution of the product spotted on an acidic clay phenolic resin developed an orange-colored image.

EXAMPLE 3

A mixture of 5.4 g of an isomeric mixture of 2,4-bis[(1-ethyl-2-methylindol-3-yl)carbonyl]-1,5-benzenedicarboxylic acid and 2,5-bis[(1-ethyl-2-methylindol-3-yl)carbonyl]-1,4-benzenedicarboxylic acid, prepared in a manner similar to that described in Example 1, part A above, 4.3 g of N-(4-ethoxyphenyl)aniline, 10.0 ml of acetic acetic anhydride and 2.0 ml of pyridine was stirred approximately one hour at ambient temperature. Slowly, 20.0 ml of isopropyl alcohol and 30.0 ml of ligroin were added to the mixture. A gummy product which separated was collected by decantation, and recrystallized from isopropyl alcohol to obtain 2.3 g of the isomeric mixture of 3,7-bis(1-ethyl-2-methylindol-3-yl)-3,7-bis(N-4-ethoxyphenyl-N-phenyl)-amino pyromellitide (Formula I: $R=4$-$C_2H_5O$; $R^o=R^1=R^2=H$; $Y=1$-$C_2H_5$-2-$CH_3$-indol-3-yl) and 3,5-bis-(1-ethyl-2-methylindol-3-yl)-3,5-bis(N-4-ethoxyphenyl-N-phenyl)amino pyromellitide (Formula II: $R=4$-$C_2H_5O$; $R^o=R^1=R^2=H$; $Y-1$-$C_2H_5$-2-$CH_3$-indol-3-yl), a light brown solid, which melted 157°–160° C. A significant infrared maximum appeared at 1760 ($C=O$; s) $cm^{-1}$. A toluene solution of the product spotted on an acidic clay or a phenolic resin developed a brown-colored image.

EXAMPLE 4

A. Proceeding in a manner similar to that described in Example 1, part A above. 10.9 g of pyromellitic dianhydride and 24.2 g of N,N-dimethylaniline were interacted in the presence of 13.3 g of anhydrous aluminum chloride in 40.0 ml chlorobenzene to obtain 3.1 g of the isomeric mixture of 2,4-bis[(4-dimethylaminophenyl)carbonyl]-1,5-benzenedicarboxylic acid (Formula III: $Y=4$-$(CH_3)_2NC_6H_5$) and 2,5-bis[(4-dimethylaminophenyl)carbonyl]-1,4-benzenedicarboxylic acid (Formula IV: 4-$(CH_3)_2NC_6H_5$), a yellow solid, which melted at 273°–276° C.

B. A mixture of 0.23 g of the isomeric mixture of [2,4-bis(4-dimethylaminophenyl)carbonyl]-1,5-benzenedicarboxylic acid and [2,5-bis(4-dimethylaminophenyl)carbonyl]-1,4-benzenedicarboxylic acid from part A above, 0.4 g of di(4-octylphenyl)-amine and 0.3 ml of acetic anhydride was agitated at a temperature in the range of 40°–45° C. for approximately two hours and sat overnight at ambient temperature. The resulting solid was collected by filtration, washed with hexane and dried to obtain 0.39 g of an isomeric mixture of 3,7-bis(4-dimethylaminophenyl)-3,7-bis[N,N-di(4-octylphenyl)amino]pyromellitide (Formula I: $R=R^1=4-C_8H_{17}$; $R^o=R^2=H$; $Y=4-(CH_3)_2NC_6H_5$) and 3,5-bis(4-dimethylaminophenyl)-3,5-bis[N,N-di(4-octylphenyl)amino]-pyromellitide (Formula II: $R=R^1=4-C_8H_{17}$; $R^o=R^2=H$; $Y=4-(CH_3)_2NC_6H_5$), a pale yellow solid, which melted at 195°–197° C. A significant infrared maximum appeared at 1760 (C=O; s) cm$^{-1}$. An ultraviolet maximum appeared at 255 millimicrons. A toluene solution of the product spotted on an acidic clay or a phenolic resin developed a red-orange image.

EXAMPLE 5

Following a procedure similar to that described in Example 4, part B, 0.92 g of an isomeric mixture of [2,4-bis(4-dimethylaminophenyl)carbonyl]-1,5-benzenedicarboxylic acid and [2,5-bis(4-dimethylaminophenyl)carbonyl]1,4-benzenedicarboxylic acid, 0.72 g diphenylamine were interacted in 8.0 ml of acetic anhydride to obtain 1.1 g of an isomeric mixture of 3,7-bis(4-dimethylaminophenyl)-3,7-bis(diphenylamino)pyromellitide (Formula I: $R=R^o=R^1=R^2=H$; $Y=4-(CH_3)_2NC_6H_5$) and 3,5-bis(4-dimethylaminophenyl)-3,5-bis(diphenylamino)pyromellitide (Formula II: $R=R^o=R^1=R^2=H$; $Y=4(CH_3)_2NC_6H_5$) which melted at 196°–199° C. (dec.). The nuclear magnetic resonance spectrum consistent with the assigned structure. An infrared maximum appeared at 1770 (C=O; s) cm$^{-1}$. An ultraviolet maxima appeared at 237 millimicrons. A toluene solution of the product spotted on an acidic cly or phenolic resin developed an orange-colored image.

EXAMPLE 6

A. Proceeding in a manner similar to that described in Example 1, part A above, 9.0 g of N,N-diethylaniline and 5.5 g of pyromellitic dianhydride were interacted in 100.0 ml of toluene in the presence of 16.0 g of anhydrous aluminum chloride to obtain an isomeric mixture of [2,4-bis(4-diethylaminophenyl)-carbonyl]-1,5-benzenedicarboxylic acid (Formula III: $Y=4-(C_2H_5)_2NC_6H_5$) and [2,4-bis(4-diethylaminophenyl)carbonyl]-1,5-benzenedicarboxylic acid (Formula IV: $Y=4(C_2H_5)_2NC_6H_5$), a yellow solid.

B. In amanner similar to that described in Example 4, part B above, a mixture of 0.49 g of an isomeric mixture of [2,4-bis(4-diethylaminophenyl)carbonyl]-1,5-benzenedicarboxylic acid and [2,5-bis(4-diethylaminophenyl)carbonyl]-1,4-benzenedicarboxylic acid from part A above and 0.80 g di(4-octylphenyl)amine was interacted in 4.0 ml of acetic anhydride at 45°–50° C. to obtain 1.0 g of an isomeric mixture of 3,7-bis(4-diethylaminophenyl)-3,7-bis[N,N-di(4-octylphenyl)amino]pyromellitide (Formula I: $R=R^1=4-C_8H_{17}$; $R^o=R^2=H$; $Y=4-(C_2H_5)_2NC_6H_5$) and 3,5-bis(4-diethylaminophenyl)-3,5-bis[N,N-di(4-octylphenyl)amino]pyromellitide (Formula II: $R=R^1=4-C_8H_{17}$; $R^o=R^2=H$; $Y=4-(C_2H_5)_2NC_6H_5$), a red-brown-colored solid, which melted over the range 88°–96° C. The nuclear magnetic resonance spectrum was concordant with the assigned structure. An infrared maximum appeared at 1790 (C=O; s) cm$^{-1}$. An ultrviolet maximum appeared at 241 millimicrons. A toluene solution of the product spotted on an acidic clay or phenolic resin developed an orange-colored image.

EXAMPLE 7

Following a procedure similar to that described in Example 6, part B above, but substituting 0.34 g of diphenylamine for 0.80 g of di(4-octylphenyl)amine, there was obtained 0.3 g of an isomeric mixture of 3,7-bis(4-diethylaminophenyl)-3,7-bis(diphenylamino)pyromellitide (Formula I: $R=R^o=R^1=R^2=H$; $Y=4-(C_2H_5)_2NC_6H_5$) and 3,5-bis(4-diethylaminophenyl)-3,5-bis(diphenylamino)pyromellitide (Formula II: $R=R^o=R^1=R^2=H$; $Y=4-(C_2H_5)_2NC_6H_5$), an orange-colored solid, which melted over the range of 135°–142° C. The nuclear magnetic resonance spectrum was in agreement with the assigned structure. An infrared maximum appeared at 1760 (C=O; s) cm$^{-1}$. The ultraviolet maximum appeared at 271 millimicrons. A toluene solution of the product spotted on an acidic clay or phenolic resin developed an orange-colored image.

EXAMPLE 8

Proceeding in a manner similar to that described in Example 6, part B above, 0.5 g of an isomeric mixture of 2,4-[bis(4-diethylaminophenyl)carbonyl]-1,5-benzenedicarboxylic acid and 2,5-[bis(4-diethylaminophenyl)carbonyl]1,4-benzenedicarboxylic acid and 0.28 g of N-(3-chlorophenyl)aniline were interacted in 2.0 ml of acetic anhydride to obtain ob 1.0 g of an isomeric mixture of 3,7-bis(4-diethylaminophenyl)-3,7-bis[N-3-chlorophenyl-N-phenyl)amino]pyromellitide (Formula I: $R=3-Cl$; $R^o=R^1=R^2=H$; $Y=4-(C_2H_5)_2NC_6H_5$) and 3,5-bis(4-diethylaminophenyl)-3,5-bis[(N-3-chlorophenyl-N-phenyl)amino]pryromellitide (Formula II: $R=3-Cl$; $R^o=R^1=R^2=H$; $Y=4-(C_2H_5)_2NC_6H_5$), an orange-colored solid, which melted over the range of 157°–173° C. An infrared maximum appeared at 1765 (C=O; s) cm$^{-1}$. An ultraviolet maximum appeared at 271 millimicrons. A toluene solution of the product spotted on an acidic clay or phenolic resin developed on orange-colored solid.

It is contemplated that by following the procedure described in Example 1, part A above, but using in place of 1-ethyl-2-methylindole the appropriate 1R$^6$-2-R$^7$-indole there will be obtained the following benzenedicarboxylic acids, 2,5-bis(1-R$^6$-2-R$^7$-indol-3-yl)carbonyl-1,4-benzenedicarboxylic acids and 2,4-bis(1-R$^6$-2-R$^7$-indol-3-yl)carbonyl-1,5-benzenedicarboxylic acids and mixtures thereof of Formulas III and IV wherein Y is 1-R$^6$-2-R$^7$-indol-3-yl described in Table A hereinbelow.

TABLE A

Bis(indolylcarbonyl)benzenedicarboxylic Acids

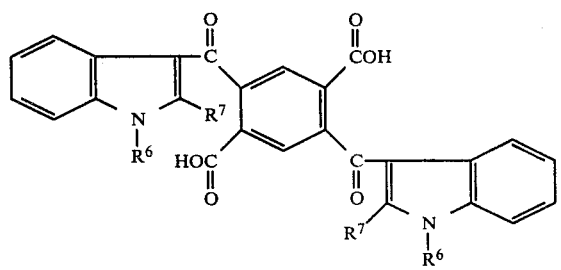

and

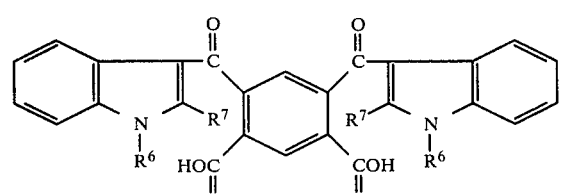

| Example | R⁶ | R⁷ |
|---|---|---|
| 9 | H | H |
| 10 | CH₃ | H |
| 11 | n-C₄H₉ | CH₃ |
| 12 | H | CH₃ |
| 13 | n-C₁₈H₁₇ | CH₃ |
| 14 | H | C₆H₅ |
| 15 | CH₃ | CH₃ |
| 16 | H | C₂H₅ |
| 17 | i-C₃H₇ | H |
| 18 | CH₃ | C₂H₅ |
| 19 | n-C₆H₁₃ | H |
| 20 | n-C₁₂H₂₅ | CH₃ |
| 21 | H | i-C₃H₇ |
| 22 | i-C₅H₁₁ | H |
| 23 | 1-i-C₈H₁₇ | CH₃ |

It is contemplated that by following the procedure described in Example 4, part A above, but using in place of N,N-dimethylaniline the appropriate 3-R⁵-N-R³-N-R⁴-aniline there will be obtained the following benezenedicarboxylic acids selected from the group consisting of 2,5-bis(2-R⁵-4-NR³R⁴-phenyl)carbonyl-1,4-benezenedicarboxylic acids and 2,4-bis(2-R⁵-4-NR³R⁴-phenyl)carbonyl-1,5-benzenedicarboxylic acids and mixtures thereof of Formulas III and IV wherein Y is 2-R⁵4-NR³R⁴-phenyl described in Table B hereinbelow.

TABLE B

Bis[(disubstituted aminophenyl)carbonyl]-benzenedicarboxylic Acids

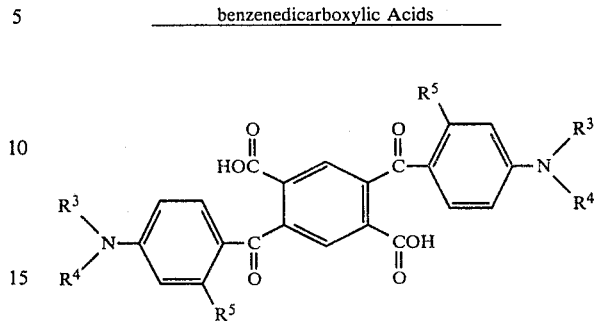

and

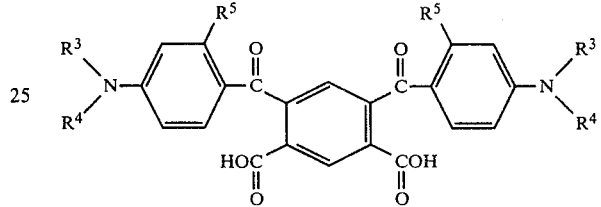

| Example | R³ | R⁴ | R⁵ |
|---|---|---|---|
| 24 | n-C₄H₉ | n-C₄H₉ | H |
| 25 | C₂H₅ | C₂H₅ | OC₂H₅ |
| 26 | C₆H₅CH₂ | C₂H₅ | H |
| 27 | C₂H₅ | C₂H₅ | CH₃ |
| 28 | C₂H₅ | C₂H₅ | OCH₃ |
| 29 | CH₃ | CH₃ | Br |
| 30 | n-C₄H₉ | n-C₄H₉ | F |
| 31 | 4-ClC₆H₄CH₂ | CH₃ | C₂H₅ |
| 32 | i-C₃H₇ | i-C₃H₇ | Cl |
| 33 | 3-CH₃C₆H₄CH₂ | s-C₄H₉ | H |
| 34 | C₂H₅ | C₂H₅ | i-C₃H₇ |
| 35 | i-C₃H₇ | CH₃ | H |
| 36 | s-C₄H₉ | s-C₄H₉ | H |
| 37 | n-C₃H₇ | C₂H₅ | H |

It is contemplated that by following the procedure described in the foregoing examples but employing the appropriate benezenedicarboxylic acids of Formulas III and IV and mixtures thereof and the appropriate substituted diphenylamine of Formula V there will be obtained pyromellitides selected from the group consisting of 3,7-bis(Y)-3,7-bis[N-(R,Rᵒphenyl)-N-(R¹, R²-phenyl)amino]pyromellitide and 3,5-bis(Y)-3,5-bis[N-(R, Rᵒ-phenyl)-N-(R¹, R²-phenyl)amino]pyromellitide and mixtures thereof of Formulas I and II, Examples 37–65, presented in Table C hereinbelow.

TABLE C
Pyromellitides of Formulas I and II

Formula I  Formula II

| Example | Y | R | R$^o$ | R$^1$ | R$^2$ |
|---|---|---|---|---|---|
| 38 | indol-3-yl | H | 3-CH$_3$ | H | H |
| 39 | 1-methylindol-3-yl | 4-i-C$_3$H$_7$ | H | H | H |
| 40 | 1-n-butyl-2-methylindol-3-yl | 4-OH | H | H | H |
| 41 | 2-methylindol-3-yl | 5-C$_9$H$_{19}$ | 3-C$_2$H$_5$ | 5-C$_9$H$_{19}$ | 3-C$_2$H$_5$ |
| 42 | 1-n-octyl-2-methylindol-3-yl | H | 3-Cl | H | H |
| 43 | 2-phenylindol-3-yl | 4-(CH$_3$)$_2$N | H | H | H |
| 44 | 1,2-dimethylindol-3-yl | H | 2-COOCH$_3$ | H | H |
| 45 | 2-ethylindol-3-yl | 4-(CH$_3$)$_2$N | H | 4-(CH$_3$)$_2$N | H |
| 46 | 1-i-propylindol-3-yl | 4-CH$_3$CONH | H | H | H |
| 47 | 1-methyl-2-ethylindol-3-yl | 4-CH$_3$CONH | H | 4-CH$_3$CONH | H |
| 48 | 1-n-hexylindol-3-yl | 4-(C$_2$H$_5$)$_2$N | H | 4-(C$_2$H$_5$)$_2$N | H |
| 49 | 1-n-dodecyl-2-methylindol-3-yl | 4-(C$_2$H$_5$)$_2$N | H | 4-(CH$_3$)$_2$N | H |
| 50 | 2-i-propylindol-3-yl | H | 2-C$_2$H$_5$ | H | H |
| 51 | 1-i-amylindol-3-yl | H | 3-I | H | H |
| 52 | 1-i-octyl-2-methylindol-3-yl | 4-Br | H | H | H |
| 53 | 4-di-n-butylaminophenyl | H | 2-CH$_3$ | 4-CH$_3$O | H |
| 54 | 2-ethoxy-4-diethylaminophenyl | H | 3-Br | 5-Br | H |
| 55 | 4-N—benzyl-N—ethylaminophenyl | H | 2-F | H | H |
| 56 | 2-methyl-4-diethylaminophenyl | H | 2-Cl | 4-F | H |
| 57 | 2-methoxy-4-diethylaminophenyl | H | 3-CH$_3$O | H | 3-CH$_3$O |
| 58 | 2-bromo-4-dimethylaminophenyl | 4-CH$_3$ | 2-CH$_3$ | 4-CH$_3$ | 3-CH$_3$ |
| 59 | 2-fluoro-4-di-n-butylaminophenyl | H | 4-n-C$_4$H$_9$O | H | 4-n-C$_4$H$_9$O |
| 60 | 2-ethyl-4-N—(4-chlorobenzyl)-N—methylaminophenyl | 4-Cl | 2-Cl | 4-Cl | 2-Cl |
| 61 | 2-chloro-4-di-i-propylaminophenyl | 4-n-C$_6$H$_{13}$ | H | H | H |
| 62 | 4-N—(3-methylbenzyl)-N—s-butylaminophenyl | 4-NHSO$_2$C$_6$H$_5$ | H | H | H |
| 63 | 2-i-propyl-4-diethylaminophenyl | 4-NHSO$_2$(4-CH$_3$C$_6$H$_4$) | H | H | H |
| 64 | 4-N—methyl-N—i-propylaminophenyl | 4-NH$_2$ | H | 4-NH$_2$ | H |
| 65 | 4-di-s-butylaminophenyl | 4-NHC$_6$H$_{11}$ | H | H | H |
| 66 | 4-N—ethyl-N—propylaminophenyl | 4-NHC$_4$H$_9$ | H | 4-NHC$_4$H$_9$ | H |

EXAMPLE 67

The use of the pyromellitide compounds of Formulas I and II and described in Examples 1 through 8 and 37 through 65 as color forming components in pressure-sensitive microencapsulated copying system is illustrated with reference to the product of Example 2.

A. A mixture of 60.0 ml of distilled water and 7.5 g of pigskin gelatin was stirred at approximately 50° C. for approximately one hour. There was added to the mixture a warmed (approximately 50° C.) solution of 30.0 g of alkylated biphenyls and 0.73 g of an isomeric mixture of 3,7-bis(1-ethyl-2-methylindol-3-yl)-3,7-bis(diphenylamino)pyromellitide and 3,5-bis(1-ethyl-2-methylindol-3-yl)-3,5-bis(diphenylamino)pyromellitide prepared as described above in Example 2. The resulting solution was stirred for approximately two minutes. A second solution of 100.0 ml of distilled water and 2.5 g of carboxymethylcellulose was prepared and warmed to approximately 50° C. for approximately one hour.

B. The two solutions, the first containing water, gelatin, alkylated biphenyls and the product, and the second containing water with carboxymethylcellulose were mixed by means of an Eppenbach Homo-Mixer (Gifford-Wood Co., Hudson, N.Y.). The pH was adjusted to 6.5 by the addition of approximately 0.7 ml of 5 percent aqueous sodium hydroxide. To the resultant mixture 335.0 ml of distilled water which had been heated to 50° C. was added over a period of two to three minutes. With the stirrer running at an applied voltage of between 35 to 40 volts there was added sufficient ten percent aqueous acetic acid to set the pH at 4.5, this being the point where coacervation was initialed. After approximately five minutes, an external ice-water bath was placed around the reactor containing the suspension. Cooling was continued and at approximately 15° C., 5.0 ml of glutaraldehyde was added over a period of five minutes. When the internal temperature reached 10° C., the Eppenback Homo-Mixer was replaced with a conventional blade type laboratory agitator and the thus prepared suspension of microcapsules was stirred overnight during which period of time the temperature was allowed to warm to room temperature. In the morning 4.0 g of water was added and stirring continued for a combined total of 24 hours.

C. The microcapsule suspension prepared as described in part B above was coated on paper sheets to a thickness of approximately 0.0015 inch and the coated paper air dried. The paper thus coated with the microencapsulated colorless precursor was assembled as the top sheet in a manifold system by positioning the coated side in contact with the coated side of a commercially available receiving sheet coated with a color developer of the electron accepting type. More specifically, papers coated with a phenolic resin and with an acidic clay were employed in this test. An image was then drawn with a stylus on the top sheet bearing the microencapsulated colorless precursor on its reverse side causing the affected microcapsules to rupture thus allowing the solution of the colorless precursor held by said microcapsules to flow into contact with the color developing substance on the receiving sheet whereupon a deep orange-colored image promptly formed.

EXAMPLE 68

The utility of the pyromellitides of Formulas I and II whose preparations are described in the foregoing examples as color forming components in thermal marking systems is illustrated by the incorporation and testing of the compounds of Example 2, in a thermal sensitive marking paper. The test paper was prepared by a procedure similar to that described in U.S. Pat. No. 3,539,375.

A. A mixture of 2.0 g of an isomeric mixture of 3,7-bis(1-ethyl-2-methylindol-3-yl)-3,7-bis(diphenylamino)-pyromellitide and 3,5-bis(1-ethyl-2-methylindol-3-yl)-3,5-bis(diphenylamino)pyromellitide prepared as described in Example 2, 8.6 g of a ten percent aqueous solution of polyvinyl alcohol (approximately 99 percent hydrolyzed), 3.7 g of water and 31.6 g of 1/16 inch diameter zirconium grinding beads was charged into a container which was placed in a mechanical shaker. Shaking was effected for one hour and the zirconium beads were removed by straining the mixture through a No. 40 sieve.

B. Similarly, a mixture of 9.8 g of 4,4'-isopropylidine diphenol (Bisphenol A), 42.0 g of a ten percent aqueous polyvinyl alcohol solution (approximately 99 percent hydrolyzed), 18.2 g of water and 221.2 g of 1/16 inch diameter zirconium grinding beads was charged into a container which was placed in a mechanical shaker. After shaking was effected for one hour, the zirconium beads were removed by straining through a No. 40 sieve.

C. A coating composition was prepared by mixing 2.1 g of the slurry from part A above and 47.9 g of the slurry from part B above. The mixture was uniformly coated on sheets of paper at thicknesses of approximately 0.0015 inch and the coated sheets air-dried. The coated paper was tested by tracing a design on the coated side of the paper placed on a smooth flat surface with a stylus heated to approximately 125° C. A deep orange-colored image corresponding to the traced design promptly developed.

What is claimed is:

1. A compound selected from the group consisting of 3,7-bis(Y)-3,7-bis[N-(R, $R^o$-phenyl)-N-($R^1$, $R^2$-phenyl)amino]pyromellitide having the formula

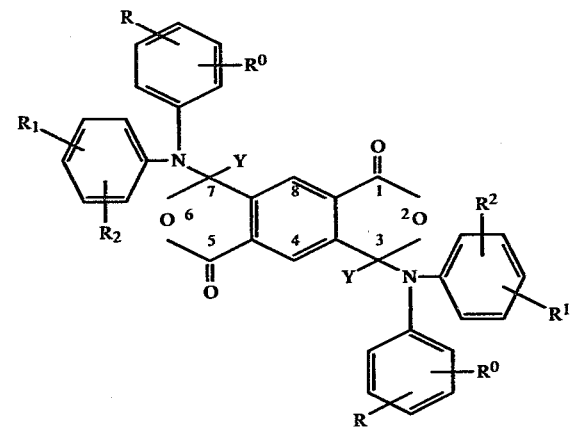

and 3,5-bis(Y)-3,5-bis[N-(R, $R^o$-phenyl)-N-($R^1$, $R^2$-phenyl)amino]pyromellitide having the formula

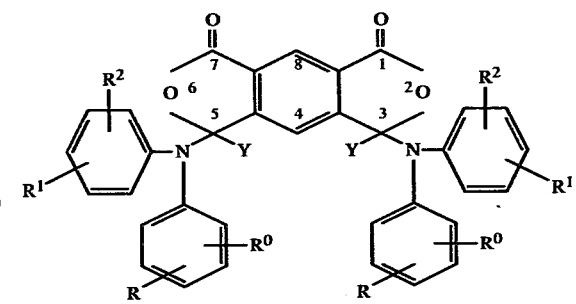

and mixtures thereof wherein:

R, $R^o$, $R^1$ and $R^2$ are the same or different and are selected from the group consisting of hydrogen, halo, hydroxyl, $C_1$ to $C_4$ alkoxy, non-tertiary $C_1$ to $C_9$ alkyl, COOZ and $NZ^1Z^2$ where Z and $Z^1$ are hydrogen or non-tertiary $C_1$ to $C_4$ alkyl and $Z^2$ is hydrogen, non-tertiary $C_1$ to $C_4$ alkyl, $C_5$ to $C_7$ cycloalkyl, $C_1$ to $C_4$ alkanoyl, phenylsulfonyl or phenylsulfonyl substituted by non-tertiary $C_1$ to $C_4$ alkyl;

Y is a radical selected from the group consisting of

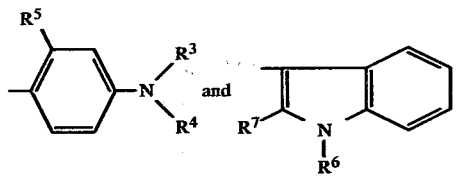

in which $R^3$ and $R^4$ are the same or different and are selected from the group consisting of non-tertiary $C_1$ to $C_4$ alkyl, benzyl, and benzyl substituted by one or two of halo, $C_1$ to $C_4$ alkyl, $C_1$ to $C_4$ alkoxy or nitro;

$R^5$ is selected from the group consisting of hydrogen, non-tertiary $C_1$ to $C_4$ alkyl, halo and $C_1$ to $C_4$ alkoxy;

$R^6$ is selected from the group consisting of hydrogen and non-tertiary $C_1$ to $C_{12}$ alkyl; and $R^7$ is selected from the group consisting of hydrogen, non-tertiary $C_1$ to $C_4$ alkyl and phenyl.

2. A compound selected from the group consisting of 3,7-bis(1-$R^6$-2-$R^7$-indol-3-yl)-3,7-[N-(R, $R^o$-phenyl)-N-($R^1$, $R^2$-phenyl)amino]pyromellitide and 3,5-bis(1-$R^6$-2-$R^7$-indol-3-yl)3,5-bis[N-(R, $R^o$-phenyl)-N-($R^1$, $R^2$-phenyl)amino]pyromellitide and mixtures thereof according to claim 1 wherein Y represents 1-$R^6$-2-$R^7$-indol-3-yl and R, $R^o$, $R^1$, $R^2$, $R^6$ and $R^7$ each have the same respective meanings given in claim 1.

3. 3,7-Bis(1-ethyl-2-methylindol-3-yl)-3,7-bis[N-phenyl-N-(4-ethoxyphenyl)amino]pyromellitide according to claim 2.

4. 3,5-Bis(1-ethyl-2-methylindol-3-yl)-3,5-bis[N-phenyl-N-(4-ethoxyphenyl)amino]pyromellitide according to claim 2.

5. 3,7-Bis(1-ethyl-2-methylindol-3-yl)-3,7-bis[di(4-octylphenyl)amino]pyromellitide according to claim 2.

6. 3,5-Bis(1-ethyl-2-methylindol-3-yl)-3,5-bis[di(4-octylphenyl)amino]pyromellitide according to claim 2.

7. 3,7-Bis(1-ethyl-2-methylindol-3-yl)-3,7-bis(diphenylamino)pyromellitide according to claim 2.

8. 3,5-Bis(1-ethyl-2-methylindol-3-yl)-3,5-bis(diphenylamino)pyromellitide according to claim 2.

9. A compound selected from the group consisting of 3,7-bis(2-$R^5$-4-$NR^3R^4$-phenyl)-3,7-bis[N-(R, $R^o$-phenyl)-N-($R^1$, $R^2$-phenyl)amino]pyromellitide and 3,5-bis(2-$R^5$-4-$NR^3R^4$phenyl)-3,5-bis[N-(R, $R^o$-phenyl)-N-($R^1$, $R^2$-phenyl)amino]pyromellitide according to claim 1 wherein Y represents 2-$R^5$-4$NR^3R^4$-phenyl and R, $R^o$, $R^1$, $R^2$, $R^3$, $R^4$ and $R^5$ each have the same respective meanings given in claim 1.

10. 3,7-Bis(4-dimethylaminophenyl)-3,7-bis[di(4-octylphenyl)amino]pyromellitide according to claim 9.

11. 3,5-Bis(4-dimethylaminophenyl)-3,5-bis[di(4-octylphenyl)amino]pyromellitide according to claim 9.

12. 3,7-Bis(4-dimethylaminophenyl)-3,7-bis(diphenylamino)pyromellitide according to claim 9.

13. 3,5-Bis(4-dimethylaminophenyl)-3,5-bis(diphenylamino)pyromellitide according to claim 9.

14. 3,7-Bis(4-diethylaminophenyl)-3,7-bis[di(4-octylphenyl)amino]pyromellitide according to claim 9.

15. 3,5-Bis(4-diethylaminophenyl)-3,5-bis[di(4-octylphenyl)amino]pyromellitide according to claim 9.

16. 3,7-Bis(4-diethylaminophenyl)-3,7-bis(diphenylamino)pyromellitide according to claim 9.

17. 3,5-Bis(4-diethylaminophenyl)-3,5-bis(diphenylamino)pyromellitide according to claim 9.

18. 3,7-Bis(4-diethylaminophenyl)-3,7-bis[N-(4-chlorophenyl)-N-phenylamino]pyromellitide according to claim 9.

19. 3,5-Bis(4-diethylaminophenyl)-3,5-bis[N-(4-chlorophenyl)-N-phenylamino]pyromellitide according to claim 9.

* * * * *

UNITED STATES PATENT AND TRADEMARK OFFICE
CERTIFICATE OF CORRECTION

PATENT NO. : 4,417,059

DATED : November 22, 1983

INVENTOR(S) : Paul J. Schmidt and William M. Hung

It is certified that error appears in the above-identified patent and that said Letters Patent is hereby corrected as shown below:

Column 2, line 43, "as" should read -- at --.

Column 6, under the formula between lines 1-7, -- Formula V -- should be inserted.

Column 6, line 54, "an" should read -- as --.

Column 9, line 13, "product" should read -- produce --.

Column 11, lines 65-66, "Y=1-$C_2H_5$-2$CH_3$-$CH_3$-indol-3-yl" should read -- Y=1-$C_2H_5$-2-$CH_3$-indol-3-yl --.

Column 13, line 37, -- was -- should be inserted after "spectrum".

Column 20, line 38 and lines 63-64, both instances, -- non-tertiary -- should be inserted before "$C_1$ to $C_4$ alkoxy".

Signed and Sealed this

Eighteenth Day of March 1986

[SEAL]

Attest:

DONALD J. QUIGG

Attesting Officer

Commissioner of Patents and Trademarks